United States Patent [19]

Hamano et al.

[11] Patent Number: 5,840,054
[45] Date of Patent: Nov. 24, 1998

[54] METHOD FOR OBSTRUCTING LACRIMAL CANALICULI WITH INFUSABLE SOLUTION OR DISPERSION

[75] Inventors: Takashi Hamano, Osaka; Teruo Miyata; Takeshi Ogawara, both of Tokyo, all of Japan

[73] Assignee: Koken Co., Ltd., Tokyo, Japan

[21] Appl. No.: 493,282

[22] Filed: Jun. 21, 1995

[30] Foreign Application Priority Data

Jun. 24, 1994 [JP] Japan ................................. 6-143623

[51] Int. Cl.⁶ ............................................ A61F 9/00
[52] U.S. Cl. ................... 604/8; 604/9; 604/294; 424/548; 424/423; 424/422; 424/549; 424/484; 514/8
[58] Field of Search ................... 424/548, 423, 424/422, 549, 484; 604/8, 9, 294; 514/8

[56] References Cited

U.S. PATENT DOCUMENTS

| | | | |
|---|---|---|---|
| 3,949,750 | 4/1976 | Freeman | 128/260 |
| 4,242,291 | 12/1980 | Hughes et al. | 264/1 |
| 4,424,208 | 1/1984 | Wallace et al. | 424/177 |
| 4,592,864 | 6/1986 | Miyata et al. | 530/356 |
| 4,660,546 | 4/1987 | Herrick et al. | 128/1 |
| 4,803,075 | 2/1989 | Wallace et al. | 424/423 |
| 4,837,285 | 6/1989 | Berg et al. | 530/356 |
| 4,915,684 | 4/1990 | MacKeen et al. | 604/8 |
| 4,959,048 | 9/1990 | Seder et al. | 604/9 |
| 5,137,875 | 8/1992 | Tsunenaga et al. | 514/21 |
| 5,163,959 | 11/1992 | Herrick | 623/11 |
| 5,283,063 | 2/1994 | Freeman | 424/427 |
| 5,314,874 | 5/1994 | Miyata et al. | 514/21 |

FOREIGN PATENT DOCUMENTS

| | | |
|---|---|---|
| 0089145 | 9/1983 | European Pat. Off. |
| 0196197 | 10/1986 | European Pat. Off. |
| 0268421 | 5/1988 | European Pat. Off. |
| WO9405342 | 3/1994 | European Pat. Off. |

OTHER PUBLICATIONS

Wells et al. 1993 Ophthalwic Surgery 24:47–48.
Wallace S. Foulds, "Intra–Canalicular Gelatin Implants in the Treatment of Kerato–Conjunctivitis SICCA," British J. Ophthalmology, vol. 45, No. 9, pp. 625–627, Sep. 1961.

*Primary Examiner*—Stephen Walsh
*Assistant Examiner*—Kenneth A. Sorensen
*Attorney, Agent, or Firm*—Varndell Legal Group

[57] ABSTRACT

A method of obstructing the lacrimal canaliculi by infusing therein a solution or liquid dispersion containing a gel forming material, such having collagen as the main ingredient in the range of 1 mg/ml to 70 mg/ml for improving the symptoms of dry eye.

18 Claims, 1 Drawing Sheet

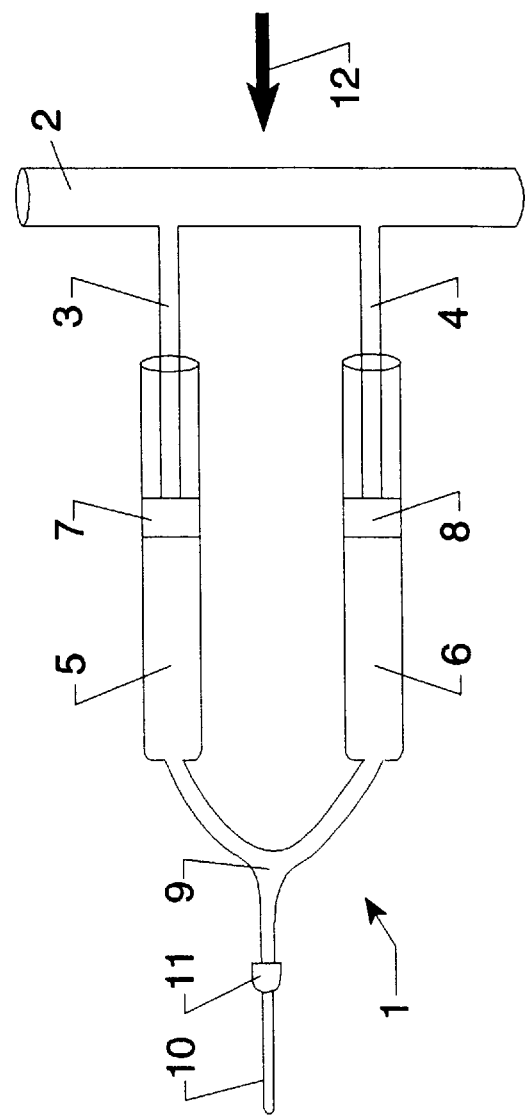

METHOD FOR OBSTRUCTING LACRIMAL CANALICULI WITH INFUSABLE SOLUTION OR DISPERSION

BACKGROUND OF THE INVENTION

1. Field of the Invention

The present invention relates to a method for obstructing the lacrimal canaliculi with an infusible solution or dispersion and resulting infusible fluid obstruent in the lacrimal canaliculi containing an infusible material as the main ingredient for improving of the symptoms of dry eye.

DESCRIPTION OF THE PRIOR ART

Tear secretion can be enhanced with various stimulus and mental impression. On the other hand, a small amount of tears is normally secreted for preventing the dryness of the eye and washing foreign bodies out of the eye. Also, tears are responsible for prevention of keratitis conjunctivitis, and other disease because of its bactericidal effect. Tears are secreted from the lacrimal glands, collected at the medial canthus, enter the lower and upper lacrimal punctum, pass through the upper and lower canaliculi, lacrimal sac and nasolacrimal duct, and drain into the nasal cavity through the inferior nasal meatus.

Recently, the number of patients with dry eyes has been increasing. The disease occurs when tear secretion is extremely deficient or lacking. The surface of the eye is therefore dry, causing pain and a failure to prevent disease.

A known method for improving the symptoms of dry eye is inserting a cylindrical plug with a conical end, 1 to 3 mm in length and 0.2 to 0.8 mm in diameter, made of aqueous or nonaqueous material and which is called a punctual plug, into the lacrimal punctum for occlusion so that the outflow of tears is prevented. When there is no tear secretion, measures such as application of artificial tears is taken in conjunction with inserting a punctual plug (see JP Patent Publication No. Sho 61-15559 or Hei 3-292953). Known punctual plugs include aqueous plugs such as copolymers of trimethylene carbonate and glycosides, or glycosides and lactides other than glycosides (JP Publication No. Hei 43-64856). These aqueous plugs (or dissolvable implants) are in solid form when used, but since these aqueous plugs readily dissolve in water, they can be absorbed by the body rather quickly, such as in approximately a two-week period. Catgut or gut suture, which is a conventional surgical suture, is also known for closing the lacrimal punctum. Nonaqueous plugs such as a copolymer of the hydrogels polyvinylpyrrolidone and polymethylmethacrylate, polytetrafluoroethylene (Teflon), silicone and stainless steel are also known. See, for example, U.S. Pat. Nos. 3,949,750 and 4,660,546, which are incorporated herein by reference.

As to conventional nonaqueous plugs, however, one end of the plug always sticks out of the lacrimal punctum, which may touch the corneal and cause damage to it. Further, such nonaqueous plugs always cause the patient to have a foreign body sensation. Moreover, nonaqueous plugs have a disadvantage in that their long-term use may increase the size of the lacrimal punctum because a plug having a little larger diameter than the lacrimal punctum is usually used. When aqueous plugs are used, they do not provide any foreign body sensation because they completely enter the canaliculus. However, it is difficult for aqueous plugs to sustain their efficacy for a long time. Moreover, in the case of any of these plugs, many types of plugs in size increments of 0.1 mm must be prepared according to the size of patients' lacrimal punctum.

SUMMARY OF THE INVENTION

As the result of the inventors' investigation for obstruents of the lacrimal canaliculi that improve these disadvantages, that are suitable for the lacrimal punctum of any size, and that have long-term efficacy for the improvement of the symptoms of dry eye without providing a foreign body sensation, the inventors found that a solution or liquid dispersion containing a gelling or infusible ingredient or ingredients as the main ingredient(s), when infused into the lacrimal punctum, occludes the lacrimal punctum for a long period of time, and that in some cases an appropriately prepared solution or liquid dispersion of gelling ingredient(s) can gel at body temperature within the lacrimal punctum, these solutions and dispersion of gelling ingredient(s) serving as a plug for the lacrimal punctum. Thus, the inventors completed the present invention. The present invention is directed toward providing an obstruent of the lacrimal canaliculi infused in the lacrimal punctum for improvement of the symptoms of dry eye.

An object of the present invention is a liquid canalicular obstruent of a solution or a liquid dispersion containing gelling or infusible material(s) as the main ingredient(s) which is infused or introduced through the lacrimal puncta into the lacrimal canaliculi. The gelling or infusing material(s) can remain in the gelled or fused condition with the lacrimal canaliculi or puncta, so that the flow of tears therethrough is blocked for a long period of time from more than at least two weeks and up to more than four weeks. In the present invention a preferred gelling or infusible material is collagen having concentrations that can be in the range of 1 mg/ml to 70 mg/ml. This canalicular obstruent containing collagen as the main ingredient can be a solution or liquid dispersion having a physiological acceptable salt concentration. Moreover, the canalicular obstruent of the present invention can contain drugs with antibacterial activity.

The canalicular obstruent of this invention occurs as a solution or liquid dispersion containing the gelling or infusible material(s) as its main ingredient(s), which material can be selected to gel at, for example, human body temperature. The use of collagen as the gelling or infusible material has the advantage of good biocompatibility with patients because its main ingredient is collagen.

Another advantage of the obstruent of the present invention is that it is liquefied (in liquid form) when infused or introduced into the lacrimal puncta, and thus preparations of various plug sizes are not required, unlike the conventional plugs. The infusing liquid can occlude the lacrimal canaliculi by itself, and in cases where desired, it can gel or otherwise solidify and occlude the canaliculi at body temperature after infusion. The patient therefore has no foreign body sensation. On the other hand, an aqueous atelocollagen solution is known to be used for internal infusion (Japan Open-laid Application No. 28936/1985). Since this solution has (1) sufficient fluidity for infusion into the body, and when exposed to biological conditions, it is equilibrated and forms collagen fibers, (2) fits to the adjacent tissue, and (3) retains a desired volume for certain time; it is used for filling and raising of tissue defects, such as for skin depressions. However, it has not been previously known that a solution of this type could improve the symptoms of dry eye when infused through the lacrimal puncta as shown in this invention.

BRIEF DESCRIPTION OF THE DRAWINGS

FIG. 1 shows a device for mixing two materials prior to injection into the lacrimal punctum.

DETAILED DESCRIPTION OF THE INVENTION

The solution or liquid dispersion of gelling or infusible material(s), the canalicular obstruent of this invention, is injectable into either the upper or lower lacrimal punctum or through the respective lacrimal punctum into either the upper or lower canaliculus by using a needle or other means. The word "infusible" as used in the specification describes a material or ingredient, such as in the form of a solution or dispersion, that can be introduced into a human body cavity, such as the lacrimal canaliculi or punctum, and once contained therein obstrudes or obstructs the body cavity. In other words, the "infusible" material or ingredient is or becomes an obstacle that blocks or closes up the lacrimal canaliculi or punctum, so that tears cannot pass therethrough. The word "gelling" as used in this specification describes a material or ingredient that can be in the form of an injectable solution or liquid dispersion and that is not gelled and thus capable of being injected through a needle of appropriate size to fit into the lacrimal punctum; and after injection, the "gelling" material or ingredient forms a gel to obstruct the lacrimal canaliculi or punctum, namely, prevent the passage of tears therethrough.

When collagen is used in this invention, it can be obtained from the skin, tendon, or other parts of animals, and purified collagen is preferred. Either soluble or insoluble collagen can be used, including acid-soluble collagen, salt-soluble collagen, atelocollagen, alkaline-soluble collagen, chemically-modified collagen (such as succinated, phthalated, acylated and methylated collagens) as soluble collagens, and Achilles tendon collagen, hide collagen, cross-linked collagen as insoluble collagens. The preferred concentration of this solution or liquid dispersion of collagen ranges from 1 mg/ml to 70 mg/ml. At less than 1 mg/ml, effective obstruction of the lacrimal punctum is not expected, and at more than 70 mg/ml, injection into or through the lacrimal punctum with a needle or other means is difficult. Representative solutions or liquid dispersion of collagen that can be used in the present invention include those described in U.S. Pat. Nos. 5,137,875 and 5,314,874, which are incorporated herein by reference.

When a solution or liquid dispersion of gelling or infusible material as a canalicular obstruent is introduced into through the lacrimal punctum with a needle or other means, a neutral solution or liquid dispersion is recommended, although any solution that does not provide eye irritation can be used. For example, when collagen is used as the gelling material, it is dissolved or dispersed in a physiological acceptable medium, so as to have a pH of from about 6.5 to about 8.0 and an osmolality of from about 230 to about 320 mOsm/KgH$_2$O.

Of collagens, collagens having the same isoelectric point as the human body, such as acid-soluble collagen, salt-soluble collagen, and atelocollagen, occur as a liquid at low temperature under neutral and physiological salt concentration conditions. These collagens, however, gel when heated to near body temperature, enhancing their occluding or blocking effect.

Additives can be added to the infusible solution or liquid dispersion. These additives can include ingredients having high affinity for the body, such as mucopolysaccharides including hyaluronic acid and chondroitin. Drugs having antibacterial activity (antibacterial agent) can also be mixed with the infusible solution or liquid dispersion for preventing infection. When collagen is used as the infusing ingredient, it is preferred that collagen make up more than 30% by weight of the mixture.

After infusing the solution or liquid dispersion of the present invention into the lacrimal puncta using a needle for washing of the lacrimal sac or other means, the eye should be closed and kept at rest for a few minutes to obtain an immediate puncta occluding effect. A conventional plug may be concurrently used, such as until the infusible solution or dispersion occludes the lacrimal puncta.

Materials or ingredients other than the collagen discussed above can be used as the infusible material in the form of a solution or liquid dispersion in the same manner as the solution or liquid dispersion of collagen described above. The solutions or liquid dispersions containing these other infusible materials should be physiological acceptable mediums along the guidelines for a solution or liquid dispersion of collagen discussed above. It is preferable that these other materials form a gel when injected into the lacrimal punctum. Other such infusible materials include gelatin and agarose. Gelatin or agarose can be used at a concentration of about 5 to about 300 mg/ml, and such a solution or dispersion thereof can be formulated so as to not gel or fuse at a warm temperature (i.e., about 45° C.), but gel or fuse at the body temperature of a human (i.e., about 37° C.). In other words, a solution or liquid dispersion of gelatin or agarose is maintained at a temperature above its gelling point and injected through the lacrimal punctum at this temperature; whereupon after the solution or liquid dispersion is injected and cools down to body temperature, it forms a gel that blocks tear flow.

In addition, the infusible solution or dispersion of the present invention can comprise a mixture of two materials, which themselves may not form a gel, but which form a gel or other obstruent when mixed together. A representative of such an infusible mixture is a fibrin sealant. A typical fibrin sealant that forms a gel or other obstruent is a mixture prepared by mixing fibrinogen (at a concentration of about 90 mg/ml) and thrombin (at a concentration of about 4 to about 500 IU/ml). "IU" represents International Units. An International Unit is an internationally agreed upon standard, as measured by bioassay, to which samples of a substance, such as a drug or hormone, are compared to ascertain their relative potency. The IU for thrombin is well known in the art.

Two other materials that form a gel when mixed together and can be used in accordance with the present invention are a polysaccharide, such as alginic acid, and a calcium salt solution, such as those containing CaCl$_2$. The viscosity or amounts of the polysaccharide and calcium salt are variable based on the molecular weight of the polysaccharide. A typical mixture contains polysaccharide in a concentration of about one to about 300 mg/ml and calcium salt in a concentration of about 10 to about 100 mg/ml.

If two material are mixed together that form a gel, a gelling or other obstruent mixture upon mixing, a device 1 such as shown in FIG. 1 or another device of similar function can be used to mix the materials together, such as just prior to injection. The device 1 can include a handle 2 having two arms 3,4 respectively projecting into test tubes or cylindrical-shaped holders 5,6. Each arm 3,4 has a respective plunger 7,8 secured to the end thereof. The cylinders or test tubes 5,6 are joined together by a Y-shaped tubular joint 9 that is joined to a needle 10 by a grommet 11. In practice the assembly of the handle (2), arms (3,4) and plungers (7,8) can be removed from the test tubes 5,6. The two materials that form a gel when mixed together at, for example, the body temperature of a human or at room temperature, are respectively placed in test tubes 5,6. The assembly of the handle (2), arms (3,4) and plungers (7,8) is then arranged so that the plungers (7,8) respectively hold or confine the two materials in the test tubes (5,6). When the handle is thereafter pressed in the direction of arrow 12, the two materials are mixed in the Y-shaped tubular joint 9 and the gel, gelling or other obstruent mixture is then ejected from the needle 10 for use, such as for injection into the lacrimal punctum.

In addition, any of these other infusible materials can be used in a mixture with the collagen as described above to form an infusible solution or dispersion in accordance with the present invention.

The following examples are directed to an infusible solution or dispersion containing collagen as a main ingredient and are set forth below only as representative infusible solutions or liquid dispersions for illustrating the present invention. These examples do not limit the scope of the invention in any way, especially the use of infusible solutions or liquid dispersions of materials other than collagen.

EXAMPLE 1

A neutral solution of atelocollagen with the physiological salt concentration of Koken Atelocollagen Implant (3% by weight solution of atelocollagen, pH 7.3, 260 mOsm/kgH$_2$O, manufactured by Koken, Co., Ltd, Japan) was injected into the patient's lacrimal puncta using a needle for washing of the lacrimal sac. The amount of the solution injected was about 0.1 ml per lacrimal punctum. Following closing the eyes and keeping at rest for about 10 minutes after infusion, the symptoms of dry eye were improved, and this effect persisted for more than 4 weeks.

EXAMPLE 2

The symptoms of dry eye were improved by infusing injectable collagen cross linked with an aqueous polyepoxy compound into the lacrimal puncta following the procedures of Example 1 above. The injectable collagen in the form of an aqueous dispersion was obtained by the procedures in Example 1 of U.S. Pat. No. 5,314,874, and contained 6% by weight of atelocollagen (60 mg/ml) having an ε-amino group modifying rate of cross linked atelocollagen of 49.2%. The results were the same as in Example 1.

EXAMPLE 3

The symptoms of dry eye were improved by infusing a 1:1 mixture of atelocollagen and hyaluronic acid into the lacrimal puncta following the procedures of Example 1 above. The mixture was prepared by the procedures in Example 1 of U.S. Pat. No. 5,137,875, and was an aqueous solution containing atelocollagen and hyaluronic acid each at 1% by weight concentration, and having a pH of 7.3 and an osmolality 260 mOsm/kgH$_2$O. The results were the same as in Example 1.

As described above, in the present invention, a solution or liquid dispersion containing gelling or infusible material(s) as the main ingredient(s) is used as a canalicular obstruent. This solution or liquid dispersion has advantages in that because it is injected in the form of liquid into the lacrimal canaliculi, unlike the conventional aqueous or nonaqueous plugs that are made of solid material; and after injection, the solution or dispersion forms a gel, a solid substance or is otherwise capable of blocking the flow of tears into the lacrimal canaliculi of the present invention. Thus, there is no need to prepare various types of plugs or preparations according to the size of patients' canaliculus. This is because the canalicular obstruent of the present invention is a liquid that occludes itself in the lacrimal canaliculi, and in cases where desired, it is solidified at body temperature and, therefore, has a long-term improvement effect on the symptoms of dry eye without providing any foreign body sensation.

What we claimed is:

1. A method for occluding a lacrimal canaliculi comprising injecting a solution into the lacrimal canaliculi, wherein the solution is physiologically acceptable, in a fluid form sufficient for injection through a needle at the time of injection, and changes in response to conditions in the lacrimal canaliculi into a solid form after injection.

2. The method according to claim 1, wherein the solution is a mixture of two materials that gel at human body temperature when mixed together.

3. The method according to claim 1, wherein the solution contains a member selected from the group consisting of collagen, gelatin, agarose, a mixture of fibrinogen and thrombin, and a mixture of polysaccharide and a calcium salt solution.

4. The method according to claim 1, wherein the solution contains collagen and a member selected from the group consisting of gelatin, agarose, a mixture of fibrinogen and thrombin, and a mixture of polysaccharide and a calcium salt solution.

5. The method according to claim 1, wherein the solution contains collagen in a range of 1 mg/ml to 70 mg/ml.

6. The method according to claim 1, wherein the solution entirely gels at body temperature.

7. The method according to claim 1, wherein the solution has a neutral pH and a physiological salt concentration.

8. The method according to claim 5, wherein the collagen is atelocollagen.

9. The method according to claim 1, wherein the solution contains an antibacterial agent.

10. The method according to claim 1, wherein the changes in response to conditions in the lacrimal canaliculi includes gelling of the solution.

11. The method according to claim 10, wherein the solution does not gel above human body temperature but gels at human body temperature.

12. The method according to claim 1, wherein the solution contains collagen in a range of 1 mg/ml to 70 mg/ml.

13. A method for occluding a lacrimal canaliculi comprising injecting a liquid dispersion into the lacrimal canaliculi, wherein the dispersion is physiologically acceptable, in a fluid form sufficient for injection through a needle at the time of injection, and changes in response to conditions in the lacrimal canaliculi into a solid form after injection.

14. The method according to claim 13, wherein the liquid dispersion does not gel above human body temperature but gels at human body temperature.

15. The method according to claim 13, wherein the liquid dispersion contains collagen in a range of 1 mg/ml to 70 mg/ml.

16. The method according to claim 15, wherein the liquid dispersion has a pH of abut 6.5 to about 8.0 and an osmolality from about 230 to about 320 mOsm/KgH$_2$O.

17. The method according to claim 13, wherein the liquid dispersion contains a member selected from the group consisting of collagen, gelatin, agarose, a mixture of fibrinogen and thrombin, and a mixture of polysaccharide and a calcium salt solution.

18. The method according to claim 13, wherein the liquid dispersion contains collagen and a member selected from the group consisting of gelatin, agarose, a mixture of fibrinogen and thrombin, and a mixture of polysaccharide and a calcium salt solution.

* * * * *